(12) United States Patent
Moore

(10) Patent No.: US 11,911,533 B2
(45) Date of Patent: Feb. 27, 2024

(54) TISSUE REPAIR LAMINATES

(71) Applicant: POLYNOVO BIOMATERIALS PTY LIMITED, Port Melbourne (AU)

(72) Inventor: Timothy Graeme Moore, Port Melbourne (AU)

(73) Assignee: POLYNOVO BIOMATERIALS PTY LIMITED, Port Melbourne (AU)

(*) Notice: Subject to any disclaimer, the term of this patent is extended or adjusted under 35 U.S.C. 154(b) by 0 days.

(21) Appl. No.: 16/625,046

(22) PCT Filed: Dec. 21, 2018

(86) PCT No.: PCT/AU2018/051381
§ 371 (c)(1),
(2) Date: Dec. 20, 2019

(87) PCT Pub. No.: WO2019/119057
PCT Pub. Date: Jun. 27, 2019

(65) Prior Publication Data
US 2020/0376158 A1    Dec. 3, 2020

(30) Foreign Application Priority Data
Dec. 22, 2017  (AU) ................. 2017905177

(51) Int. Cl.
*A61L 27/18* (2006.01)
*A61L 27/58* (2006.01)
*A61L 27/56* (2006.01)
*A61L 31/06* (2006.01)
*A61L 31/16* (2006.01)
*A61L 31/14* (2006.01)
*C08G 18/10* (2006.01)
*C08G 18/73* (2006.01)
*C08J 9/228* (2006.01)
*C08J 5/18* (2006.01)
*C08G 18/42* (2006.01)
*A61F 2/08* (2006.01)
*B32B 5/18* (2006.01)
(Continued)

(52) U.S. Cl.
CPC .............. *A61L 27/18* (2013.01); *A61F 2/08* (2013.01); *A61L 27/56* (2013.01); *A61L 27/58* (2013.01); *A61L 31/06* (2013.01); *A61L 31/146* (2013.01); *A61L 31/16* (2013.01); *B32B 5/18* (2013.01); *B32B 27/065* (2013.01); *B32B 27/40* (2013.01); *C08G 18/10* (2013.01); *C08G 18/222* (2013.01); *C08G 18/4277* (2013.01); *C08G 18/73* (2013.01); *C08J 5/18* (2013.01); *C08J 9/228* (2013.01); *A61F 2002/0894* (2013.01); *A61F 2210/0076* (2013.01); *A61L 2430/30* (2013.01); *A61L 2430/34* (2013.01); *B32B 2250/03* (2013.01); *B32B 2250/24* (2013.01); *B32B 2266/0278* (2013.01); *B32B 2266/104* (2016.11); *B32B 2307/54* (2013.01); *B32B 2307/5825* (2013.01); *B32B 2307/7163* (2013.01); *B32B 2307/732* (2013.01); *B32B 2535/00* (2013.01); *C08J 2375/06* (2013.01)

(58) Field of Classification Search
CPC ........ A61L 31/146; A61L 27/58; A61L 27/56; A61L 2430/34; A61L 31/148; A61L 31/16; A61L 2420/08; B32B 27/065; B32B 27/40; B32B 5/18; B32B 2250/03; B32B 2250/24; B32B 2266/0278; B32B 2307/7163; B32B 2535/00; B32B 2266/104; B32B 27/04; B32B 2250/42; B32B 2262/0292; B32B 2307/558; B32B 2307/5825; B32B 2307/732; B32B 2307/54; B32B 5/245; B32B 2307/718; B32B 2307/72; B32B 5/022; B32B 5/024; B32B 7/04; B32B 37/144; B32B 2305/026; B32B 2305/38; B32B 2556/00; B32B 2250/02; A61F 2210/0076; A61F 2/0063; A61F 2250/0031; A61F 2250/0051; C08L 75/04; C08J 9/228; C08J 5/18; C08J 2375/06; C08J 2207/10; C08G 18/10; C08G 2230/00; B29C 55/00; B29D 7/01
See application file for complete search history.

(56) References Cited

U.S. PATENT DOCUMENTS

2009/0099600 A1* 4/2009 Moore ............... C08G 18/664
606/246
2010/0256777 A1   10/2010 Datta et al.
(Continued)

FOREIGN PATENT DOCUMENTS

CN      101896526 A    11/2010
EP       0455324 B1     6/1995
(Continued)

OTHER PUBLICATIONS

Leffell (The Basics; Chapter 18, p. 192 paragraphs 1and 2, 2000) (Year: 2000).*
(Continued)

*Primary Examiner* — Anna R Falkowitz
(74) *Attorney, Agent, or Firm* — POLSINELLI PC

(57) ABSTRACT

There are provided tissue repair laminates containing at least two biodegradable polyurethane foam layers and a polyurethane structural layer. The biodegradable polyurethane is derived from biodegradable polyols. The laminates resist shrinkage under in vivo conditions and possess desirable mechanical properties such as high tensile strength. The laminates find use in, for example, the repair of tissue or muscle wall defects.

30 Claims, 5 Drawing Sheets

(51) Int. Cl.
 *B32B 27/06* (2006.01)
 *B32B 27/40* (2006.01)
 *C08G 18/22* (2006.01)

(56) References Cited

U.S. PATENT DOCUMENTS

| | | |
|---|---|---|
| 2010/0318108 A1 | 12/2010 | Datta et al. |
| 2012/0239161 A1* | 9/2012 | Datta .................. A61L 27/18 623/23.72 |
| 2014/0044861 A1 | 2/2014 | Boey et al. |
| 2016/0081783 A1* | 3/2016 | Puckett ................ D04H 1/728 264/465 |
| 2016/0175487 A1 | 6/2016 | Deng et al. |

FOREIGN PATENT DOCUMENTS

| | | |
|---|---|---|
| WO | 0168179 A1 | 9/2001 |
| WO | 2007033418 A1 | 3/2007 |
| WO | WO-2009/043099 A1 | 4/2009 |

OTHER PUBLICATIONS

International Search Report and Written Opinion dated Mar. 25, 2019 for corresponding PCT Application No. PCT/AU2018/051381.

Chinese Office Action and Search Report issued in the corresponding Chinese Patent Application No. 201880088603.8 dated Dec. 1, 2021.

Japanese Office Action dated Oct. 3, 2022, for corresponding Japanese Application No. 2020-554330.

* cited by examiner

TISSUE REPAIR LAMINATES

CROSS-REFERENCE TO RELATED APPLICATIONS

This application is a national stage application (under 35 U.S.C. § 371) of PCT/AU2018/051381, filed Dec. 21, 2018, which claims benefit of Australian Application No. 2017905177, filed Dec. 22, 2017, which are incorporated herein by reference in their entireties.

FIELD

This disclosure relates to tissue repair laminates, particularly tissue repair laminates which may be utilized in hernia repair. The laminates comprise biodegradable polyurethane foams suitably configured for cellular infiltration.

BACKGROUND

Hernias occur when an organ pushes through a defect in muscle or tissue that holds the organ in place for example the intestines may break through a weakened area in the abdominal wall. Hernias are most common in the abdominal wall but also occur in other parts of the body such as the upper thigh, groin and navel. Inguinal (groin), hiatal (diaphragm), umbilical, abdominal and incisional hernias are commonly treated by surgical intervention.

Hernia repair often involves the use of a reinforcing means, often referred to in the art as a 'mesh', which provides strength to the site and reduces the likelihood of recurrence.

Both synthetic and biological meshes have been utilized, derived from both biodegradable and non-biodegradable materials. A variety of constructs have been used, including woven, knitted, non-woven and expanded. Examples include polypropylene, PTFE, polyester and human or porcine derived dermal matrices.

Different types of hernia have different requirements in terms of mesh strength. Meshes may be introduced laparoscopically as well as through open surgery.

One of the ways that hernia repair meshes have been classified is by weight. For example:
Ultralight ≤35 g/m$^2$
Light C 35-70 g/m$^2$
Standard C 70-140 g/m$^2$
Heavy C ≥140 g/m$^2$ Generally, biologically-derived matrices are relatively heavy and stronger and can be up to about 300 g/m$^2$ in weight. Further, ePTFE (expanded PTFE) has been used at weights up to 400 g/m$^2$.

The use of meshes is thought to dramatically reduce the incidence of hernia recurrence, perhaps by at least half. However, when it does occur, recurrent herniation often occurs at the edges of the mesh due to inadequate fixation or shrinkage of the mesh in vivo. Use of light-weight meshes may result in a higher recurrence risk due to their increased flexibility and movement. Other known risk factors for hernia recurrence include postoperative infection, seroma and haematoma.

Two-thirds of recurrences occur after three years, suggesting that a surgical error is unlikely to be the only cause of recurrence and defective collagen synthesis may be equally important. All meshes invoke a biological response due to the introduction of a foreign body which has an effect on the ratio of Type I and III collagen synthesized. Changes in this ratio may affect both tensile strength and mechanical stability of the tissue formed during the repair and may increase the risk of recurrence.

In a booklet entitled "Evidence Compendium for the Davol Hernia Repair Portfolio", Bard indicate the following:
It is estimated that there are over 1 million hernia repairs occurring annually in the United States, with a predicted rise due to increasing risk factors (e.g., age, obesity, abdominal surgery)
Recurrence rate of inguinal hernia ranges from 1.2% to almost 7%, 4% to 6% in ventral hernia; recurrence rates increase to 23.8% after the first repair
Infection rates following ventral hernia repair have been shown to range from 4% to 16%
More than 80% of ventral hernia repairs currently use mesh products, because of the improved patient outcomes
Mesh repair reduces the risk of recurrence as compared to suture repair in ventral hernia repair (2.7% vs. 8.2%) and inguinal repair (by 50 to 75%)

Shrinkage of a mesh occurs due to formation of scar tissue around the mesh. Scar tissue can shrink to about 60% of the former surface area of the wound, or more.

Heavy-weight meshes are more prone to shrinkage due to the formation of scar tissue due to the smaller pore size.

Generally, a lighter mesh with larger pore size is associated with less shrinkage, and hernia recurrence is sometimes attributed to the use of a mesh that is too small in surface area to allow for shrinkage in vivo.

In view of the foregoing a need exists for improved devices for hernia repair that include one or more of the following features:
suitable porosity for cellular infiltration
strength
minimization of shrinkage in vivo
controlled biodegradability.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

In a first aspect the present disclosure provides a multilayer tissue repair laminate comprising:
(a) two or more biodegradable polyurethane foam layers; and
(b) one or more polyurethane structural layers;
wherein the polyurethane structural layers are positioned between the foam layers; and
wherein said foam layers comprise a pore structure configured for cellular infiltration.

The tissue repair laminate of the present disclosure may possess a number of advantages including one or more of the following:
the laminate is substantially resistant to shrinkage in vivo;
the foam layers enable tissue integration;
the laminate has high mechanical strength;
the laminate is synthetic and not biologic;
the manufacturing process of the laminate does not substantially affect the tissue ingrowth ability of the foam layers; and
the laminate may degrade over time so that it need not be surgically removed.

The foam layers may comprise a thermoset polyurethane or may comprise a thermoplastic polyurethane. Preferably the foam layers comprise a thermoset polyurethane. Preferably the foam layers comprise a cross-linked polyurethane.

The structural layers may comprise a thermoset polyurethane or may comprise a thermoplastic polyurethane. Preferably the structural layers comprise a thermoplastic polyurethane.

The structural layer may comprise a biodegradable polyurethane or a non-degradable polyurethane. Preferably, the structural layer is a biodegradable polyurethane. The structural layer may be designed to degrade at a different rate to the foam layers or at substantially the same rate.

As used herein, the term 'biodegradable' refers generally to the capability of being broken down in the normal functioning of living organisms/tissue, preferably into innocuous, non-toxic or biocompatible products.

In some embodiments the foam layers may degrade faster than the structural layer. The tissue repair laminate may comprise any one or more of the following features:
  (i) a suture retention strength of greater than 20 N, or greater than 25 N, or greater than 30 N, or greater than 35 N
  (ii) an ultimate tensile strength of greater than 20 N/cm, or greater than 25 N/cm, or greater than 30 N/cm, or greater than 35 N/cm, or greater than 40 N/cm
  (iii) a ball burst strength of greater than 50 N/cm, or greater than 100 N/cm, or greater than 125 N/cm, or greater than 150 N/cm, or greater than 175 N/cm, or greater than 200 N/cm; and
  (iv) a tear resistance of greater than 10 N, or greater than 15 N or greater than 20 N.

The tissue repair laminate may shrink less than 20%, or less than 15%, or less than 10%, or less than 5%, independently, in any single surface area, after 10 days under in vivo conditions.

The tissue repair laminate may shrink less than 20%, or less than 15%, or less than 10%, or less than 5%, independently, in any single surface area, after 20 days under in vivo conditions or after 60 days under in vivo conditions, or after 90 days under in vivo conditions, or after 120 days under in vivo conditions, or after 200 days under in vivo conditions, or after 1 year under in vivo conditions, or after 2 years under in vivo conditions.

The foam layers may, independently, have a thickness between about 0.1 mm and about 10 mm, or between about 0.2 mm and about 5 mm, or between about 0.3 mm and about 3 mm, or between about 0.3 mm and about 2 mm. The foam layers may, independently, have a thickness of less than about 10 mm, or less than about 6 mm, or less than about 4 mm, or less than about 2 mm or less than about 1 mm, or less than about 0.5 mm.

Preferably, the foam layers may, independently, have a thickness between 0.3 mm and about 3 mm.

The structural layers may, independently, have a thickness between about 20 μm and about 1000 or between about 50 μm and about 500 μm, or between about 50 μm and about 400 μm.

In some embodiments the foam layers may have a thickness between about 0.3 mm and about 3 mm and the structural layers may have a thickness between about 50 μm and about 400 μm.

In some embodiments the foam layers may have a thickness between about 0.5 mm and about 2 mm and the structural layers may have a thickness between about 100 μm and about 300 μm.

In some embodiments the foam layers may have a thickness between about 0.3 mm and about 1 mm and the structural layers may have a thickness between about 100 μm and about 300 μm.

In some embodiments the foam of the foam layers may, independently, be a non-reticulated foam. In some embodiments the foam of the foam layers may, independently, be a reticulated foam. The foam of the foam layers preferably has interconnecting pores. Preferably the foam of the foam layers is a non-reticulated foam.

As used herein the term 'non-reticulated' polyurethane foam refers to a polyurethane foam which has not been subjected to a post manufacturing step to remove cell windows using either chemicals (such as alkaline solution), heat (such as controlled combustion of hydrogen and oxygen), or solvents.

In some embodiments the foam may have a density between 3 g/100 ml and 12 g/100 ml, or between 4 g/100 ml and 10 g/100 ml, or between 5 g/100 ml and 8 g/100 ml.

In some embodiments the porosity of the foam may be greater than 50%, or greater than 75%, or from 80 to 95%, or from 95 to 99.9%. It is desirable that the porosity should be as high as possible while maintaining other mechanical specifications. If the porosity is too low the pores may not interconnect. If the porosity is too high the structural integrity of the foam may be mechanically compromised.

In some embodiments the average pore size of the foams may be greater than 50 μm, or greater than 75 μm, or greater than 100 μm, or greater than 200 μm, or in the range 100 to 600 μm, or in the range 100 to 400 μm.

In some embodiments the average pore size of the foam is in the range 50 to 600 μm, or in the range 60 to 600 μm, or in the range 70 to 600 μm, or in the range 75 to 400 μm, or in the range 75 to 300 μm, or in the range 100 to 300 μm.

Preferably the average pore size of the foam is greater than 75 μm, preferably between 100 and 300 μm.

In some embodiments the tissue repair laminate may have a weight between 50 and 800 g/m$^2$, or between 100 and 600 g/m$^2$, or between 200 and 500 g/m$^2$.

In some embodiments the tissue repair laminate comprises two foam layers and a single structural layer.

In some embodiments the tissue repair laminate comprises three foam layers and two structural layers.

Other combinations are envisaged so long as the structural layers are located between foam layers, for example four foam layers and three structural layers, etc.

In some embodiments the tissue repair laminate may comprise one or more further layers disposed between the foam and the structural layers. The one or more further layers may be an adhesive layer.

In some embodiments, one or more of the structural layers may be porous. The porosity may be imparted by introducing one or more apertures in the structural layer prior to construction of the laminate. Preferably the apertures are sized to allow cellular fluid to pass therethrough, for example, from one foam layer to another. In some embodiments the apertures facilitate tissue growth through the apertures.

In some embodiments, the entire laminate may have apertures. The apertures may be introduced after assembly of the laminate. The apertures may provide a conduit through the entire laminate structure, including foam layers and structural layers.

Advantageously, the apertures may allow tissue bridging between foam layers. Such tissue bridging assists in providing structural integrity to a repair once the structural begins to degrade. Accordingly, two foam layers may be held together once the structural layer begins to degrade.

In some embodiments the size of the apertures may be between about 0.1 mm and about 5 mm, preferably between 1 mm and 5 mm.

Foam Layers

The biodegradable polyurethane foam layers may be biodegradable within a living organism to biocompatible degradation products.

The polyurethane foam layers may be in vivo degradable. The polyurethane foam layers may be degradable at temperatures between about 35° C. and about 42° C.

The polyurethane foam layers may degrade by hydrolysis. The polyurethane foam layers may degrade by hydrolysis of ester functionalities.

Foam Layer Polyols

The polyurethane foam may be derived from one or more biodegradable polyols and one or more isocyanates. Alternatively, the polyurethane foam may be derived from a mixture of one or more biodegradable polyols and one or more non-biodegradable polyols and one or more isocyanates. Preferably the biodegradable polyols are polyester polyols.

The foam may be derived from one or more biodegradable polyols having a molecular weight of less than or equal to about 2000 Daltons, or less than or equal to about 1500 Daltons, or less than or equal to about 1300 Daltons.

The biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The biodegradable polyols may have a molecular weight of less than 500 Daltons or less than 400 Daltons or less than 350 Daltons, or less than 300 Daltons.

The biodegradable polyols may be in the liquid state at 20° C. and atmospheric pressure. Alternatively, the biodegradable polyols may be in the solid state at 20° C. and atmospheric pressure. In some embodiments the polyols may in the form of a mixture of solid and liquid at 20° C.

The biodegradable polyols may be derived from one or more polyol initiators and one or more hydroxy acids, diacids or cyclic esters and combinations thereof.

In some embodiments the biodegradable polyol may be derived from one or more polyol initiators and at least one hydroxy acid.

In some embodiments the biodegradable polyol may be derived from one or more polyol initiators and at least one diacid.

In some embodiments the biodegradable polyol may be derived from one or more polyol initiators and at least one cyclic ester.

In some embodiments the biodegradable polyol may be derived from one or more polyol initiators, at least one hydroxy acid and at least one diacid.

In some embodiments the biodegradable polyol may be derived from one or more polyol initiators, at least one hydroxy acid and at least one cyclic ester.

In some embodiments the biodegradable polyol may be derived from one or more polyol initiators, at least one diacid and at least one cyclic ester.

In some embodiments the biodegradable polyol may be derived from one or more polyol initiators, at least one hydroxyl acid, at least one diacid and at least one cyclic ester.

The one or more polyol initiators may be pentaerythritol, trimethylol propane, glycerol, 1,4-butanediol, ethylene glycol, sorbitol, glucose, sucrose, 1,2-propanediol, 1,3-propanediol, pentane diol, myoinositol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof.

Non-limiting examples of hydroxy acids include l-lactic acid, d-lactic acid, d,l-lactic acid, mandelic acid, phenyllactic acid, hydroxybutyric acid, hydroxyvaleric acid or glycolic acid and combinations thereof.

Non-limiting examples of cyclic esters include ε-caprolactone, glycolide, lactide, mandelide, and ρ-dioxanone and combinations thereof. The biodegradable polyols may be prepared via a ring-opening polymerisation reaction or a condensation reaction.

Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof.

The biodegradable polyols may be prepared via a ring-opening polymerisation reaction or a condensation reaction or via both a ring-opening polymerisation reaction and a condensation reaction.

The one or more non-biodegradable polyols may be a polyether polyol. The polyether polyol may be one or more of glycerol ethoxylate, glycerol propoxylate, glycerol ethoxylate-co-propoxylate, glycerol ethoxylate-block-propoxylate, pentaerythritol ethoxylate, pentaerythritol propoxylate and trimethylolpropane propoxylate.

The one or more non-biodegradable polyols may have a molecular weight of less than or equal to about 2000 Daltons, or less than or equal to about 1500 Daltons, or less than or equal to about 1300 Daltons.

The non-biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The non-biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The non-biodegradable polyols may have a molecular weight of less than 500 Daltons or less than 400 Daltons or less than 350 Daltons, or less than 300 Daltons.

The biodegradable polyols impart biodegradability to the foam. The polyols may be prepared by condensation polymerization or ring-opening polymerization with a high proportion of initiator (or starter) to control the molecular weight. The amount of initiator may range from between 1 mole of initiator per 200 g of polyol and 1 mole of initiator per 5000 g of polyol, or between 1 mole of initiator per 500 g polyol and 1 mole of initiator per 2000 g of polyol. Non-limiting examples of suitable monomers for the initiator include pentaerythritol (4-arm), trimethylol propane (3-arm), glycerol (3-arm), 1,4-butanediol (2-arm), myo-inositol (6-arm). Mixtures of initiators may be utilized. Mixtures of polyols may be utilized. It may be preferable to minimize the number of components. However, in some instances it may be advantageous to utilise more than one polyol, or more than two. The polyol may have a hydroxyl functionality of 2 or more. Polyols having only a single hydroxyl functionality, when used in large amounts, may not result in an adequate foam. However, minor amounts may be used to adjust the properties of the foam, for example, adding a few percent of a mono-hydroxyl compound which has a long-chain lipophilic chain, may influence the hydrophobicity/hydrophilicity of the foam.

The rate of degradation of the foam layer may be controlled by altering the ratio of biodegradable polyol to that of non-biodegradable polyol. By reducing or eliminating a non-biodegradable polyol from the formulation, faster degrading foam layers may be produced which may be desirable in certain applications. Monomer selection may also influence the rate of degradation due to kinetic differences in the rate of hydrolysis of different ester linkages.

Biodegradable and non-biodegradable polyols have different functions in the foam layer of the tissue repair laminate. Non-biodegradable polyols may be selected from the polyether polyols, for example, glycerol ethoxylate, glycerol propoxylate and glycerol ethoxylate-co-propoxylate. Such non-biodegradable polyols may stabilize the foam through the introduction of non-biodegradable function. Further they may provide a mechanism to control the hydrophilic/hydrophobic balance through, for example, the ethoxylate/propoxylate content. They may also improve foam resilience by lowering the glass transition temperature (Tg).

Biodegradable polyols may be solid at lower molecular weights than non-biodegradable polyols, for example, polycaprolactone diol of 500 molecular weight is a solid at room temperature, whereas poly(propylene glycol) remains a liquid to a much higher molecular weight. High molecular weight non-biodegradable liquid polyols may act as a 'filler' to reduce the isocyanate content and hence reduce the likelihood of scorching through excessive exothermic reaction during preparation of the foams.

Biodegradable polyols may be derived from one or more polyol initiators and at least one hydroxy acid and/or cyclic ester. They may contribute to lowering the Tg in circumstances where the Tg has not been reduced sufficiently by the non-biodegradable polyether. The polyol may be a 3-arm, glycerol-initiated polyol based on ε-caprolactone and one of glycolic acid or lactic acid. The amount of the CL:(LA and/or GA) may influence both the glass transition as well as the degradation time. More caprolactone lowers the Tg and increases the degradation time. The molecular weight may be 800-1200 Daltons. The molecular weight may be low enough to be liquid, but high enough to not require high amounts of isocyanate for reaction in order to avoid scorching.

Foam Layer Isocyanates

The polyurethanes from which the foam layers are prepared may be derived from one or more biodegradable polyols and one or more isocyanates. The molar ratio of isocyanate functions to hydroxy and other isocyanate reactive functions from which the foam is derived (the isocyanate index) may be less than or equal to 1.0, or less than or equal to 0.9, or less than or equal to 0.8, or less than or equal to 0.7, or less than or equal to 0.6. The isocyanate index may be between 0.4 and 1.0, or between 0.6 and 0.9.

The polyurethane foam may be derived from polyols and isocyanates having an isocyanate content (that is, the content of NCO functions) of less than 20% by weight, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and isocyanates. The foam may have an isocyanate content of between 5% and 20%, or between 8% and 17%, or between 11% and 14% by weight based on the total weight of polyol and isocyanate.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used but may impart a higher glass transition temperature which may result in a stiffening of the foam. Combinations of isocyanates may be used and may in some instances be preferable, for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Lowering the isocyanate index results in softer and weaker foam layers which degrade more quickly. Increasing the isocyanate index may increase the degradation time but results in stronger foam layers.

A biodegradable polyurethane foam is advantageous since it may be designed to include the properties of resilience, resistance to premature degradation, resistance to contraction, prevention of excessive acidic degradation products, biocompatibility, controlled water absorption, compatibility with other polyurethane layers and ease of incorporating additives during synthesis. The foams may be soft and conformable to a desired shape.

The foams may be designed to degrade at a specific rate. They may be designed to retain structural integrity for over, for example, three months or longer, or they may be designed to retain structural integrity for as little as, for example, a few days, even one or two days.

The polyurethane foam layers may degrade, under the conditions of ASTM F1635, such that the mass of the foam layers decreases by between about 10% and about 90% in a period of one year or less.

Alternatively, the mass of the foam layers may decrease by between about 10% and about 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane foam. Accordingly, the polyurethane may be designed to degrade within a specific period of time. This is advantageous in providing materials that are partially, fully, or substantially fully degradable in a specific period of time, for example, when the functional aspects of the polyurethane foam layers are no longer required.

This is particularly useful where the polyurethane is targeted for in vivo applications, as the polyurethane may not need to be surgically removed from a patient's body.

The rate of degradation of the foam may be controlled by altering the ratio of biodegradable polyol to non-biodegradable polyol or through choice of monomers. By reducing or eliminating a non-biodegradable polyol from the formulation, faster degrading materials may be produced which may be desirable in certain applications.

The foams may be derived from at least one prepolymer which may be prepared by contacting one or more biodegradable polyols and/or one or more polyol initiators with one or more polyisocyanates. Non-limiting examples of polyol initiators are, for example, pentaerythritol, trimethylol propane, glycerol, 1,4-butanediol and myo-inositol, ethylene glycol, sorbitol, glucose, sucrose, 1,2-propanediol and mixtures thereof. The foam may be derived from a mixture of such so-formed prepolymers and further polyisocyanate. The foam may contain less than 50% by weight of prepolymer and greater than 50% by weight of polyisocyanate based on the combined weight of these components. The foam may contain from less than 30% by weight of prepolymer and greater than 70% by weight of polyisocyanate based on the combined weight of these components. Foams prepared in this way advantageously may possess high strength and fine cell structure.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

Various additives known in the fields of polyurethane foam technology and tissue engineering may be added to the foam. These additives may be added during or after synthesis of the foam. The additives in some cases may react during the foam synthesis and be incorporated covalently into the foam. Exemplary additives include antimicrobial agents, plasticizers, pore openers, antioxidants, antistatic agents, catalysts, fillers, flame retardants, softeners/flexibilisers, cell control agents, release agents, stabilizers, fillers, dyes, pigments, pigment dispersants, solvents, anaesthetics, cells, enzymes, proteins, growth factors, growth inhibitors, haemostatic agents and bioactive agents such as drugs. The additives may or may not be chemically bonded to the foam.

Catalysts

There are a large number of catalysts known in the field of polyurethane synthesis that may be used in the preparation of the polyurethanes of the present disclosure. Various catalysts may be used in the preparation of the compositions and these may provide different attributes. For example, dibutyltin dilaurate (DBTL), stannous octoate and amine-based catalysts, such as DABCO. Bismuth, zinc and titanium-based catalysts are also known to catalyze urethane formation effectively and exhibit low toxicity. COSCAT Z-22 is a zinc-based catalyst and is an example of a catalyst that can be used that has low toxicity and gives effective results. Mercury and lead-containing catalysts are effective but are considered toxic (non-biocompatible) and therefore unsuitable. Combinations of catalysts are known to be effective. Minimisation of catalyst amount is also desirable.

Surfactant

The function of the surfactant (stabilizer, foaming agent) is to assist in preventing the bubbles in the foam from bursting when they are formed during the reaction, which allows them to rise and create a stable foam which can then cure.

Surfactants may be siloxane-ether copolymers, fluoro-ether copolymers, or other amphiphilic compounds containing a hydrophobic portion and a hydrophilic portion. There are many commercial surfactants that have been specifically developed for polyurethane foams. Amounts used vary from 0.01% to 1.5% by mass of the overall formulation. Preferred amounts are in the range 0.01% to 0.20% of the formulation. The most suitable amount depends on the molecular weight of the surfactant and the composition and type, as well as the remainder of the formulation—some formulations may be more hydrophobic and some may be more hydrophilic and hence may require different amounts of stabilisation. Useful surfactants may be simple block copolymers and brush-type copolymers. It is straightforward for the skilled person to vary the concentration of surfactant and determine which concentration is most effective in stabilizing the foam layer.

Blowing Agent

The foams may be blown by any method known in the art. The blowing agent may be generated during formation of the foam and/or may be added as one or more further components. Water may be used in the formulation to react with isocyanate, thus forming a urea linkage and $CO_2$ gas. The $CO_2$ gas creates the bubbles and blows the foam. Temperature, mixing and choice of surfactant, for example, may all affect the size of the bubbles (cell size). Commercially, polyurethane foams range in pore size from microporous (low density shoe soles) through to open cell large-celled foams (for example in filters or foam mattresses). Desirable porosities may be obtained by using 0.1 to 4% by weight of water, preferably 1.0 to 1.5% by weight of water in the overall formulation. This results in an appropriate level of foaming. Less water results in a denser foam. Higher amounts of water may be useful, but there will be a limit where the mechanical properties are negatively affected and scorching becomes likely.

Pentane and other low-boiling hydrocarbons may also be suitable as blowing agents. Foams produced in this manner may be advantageously urea-free due to the absence of water. Desirably, the absence of water reduces the amount of isocyanate required to react in the formulation, which consequently reduces the amount of heat generated when the foam is produced. This is particularly advantageous in large scale preparations where the heat of reaction may be more difficult to dissipate from the foam.

The foam layers may, independently, comprise any one or more of the herein disclosed features in any combination.

Preparation of the Foam Layer Polyurethane

The foams may be simply prepared by a one-pot method. All the components may be combined and mixed with or without the application of heat, and the foam will rise and cure. Alternatively, the foams may be prepared by any of the continuous or semi-continuous processes well known in the art.

In one embodiment, one or more polyols or polyol initiators is/are first treated with a polyisocyanate to form a prepolymer. This prepolymer is in turn treated with further components so to form the foam. In another embodiment, further polyisocyanate over and above that utilized to form the prepolymer may be utilized.

In another embodiment, all components, apart from the polyisocyanate component(s) are mixed together to form one part. The polyisocyanate is then added so as to begin the reaction. This is advantageous in that the two parts are both stable prior to mixing them together.

The foam may be prepared in a solvent free process.

The foams may be advantageously prepared by a one-pot batch procedure which may require no isolation or purification of intermediate materials. The foams may be prepared from low cost raw materials.

Reticulation

In some instances it may be advantageous to reticulate the foam. Reticulation results in the removal of cell windows so as to increase the amount of open cell material. This may be advantageous when fluid transfer is a requirement. This may be performed in a special chamber (reticulation chamber) where hydrogen and oxygen are introduced to the foam and ignited to disrupt and remove any cell windows.

Cell openers or cell opening agents may be added to the foam mixture to, for example, disrupt the pore structure during the foaming process, thereby creating foams with a natural sponge structure. Cell openers may reduce the tightness and shrinkage of the foam, resulting in dimensionally stable foams with inter-connected pores. Cell openers and other reaction components of polyurethane foams are discussed, for example in Szycher, M, Szycher's Handbook of Polyurethanes, CRC Press, New York, N.Y., 9-6 to 9-8 (1999). Cell openers suitable for use include powdered divalent metal salts of long-chain fatty acids having from about 1-22 carbon atoms. Divalent metal salts of stearic acid, such as calcium and magnesium stearate, are examples of cell openers. The concentrations of cell openers in the resin mix may be in the range of approximately 0.1-7.0% by weight or in the range of approximately 0.3 to 1% by weight.

Bioactive Agents

Bioactive agents may optionally be added to the foam mix. As used herein, the term 'bioactive' refers generally to an agent, a molecule, or a compound that affects biological or chemical events in a host.

Structural Layer

The structural layer may consist of more than one layer. For example, the structural layer may be a laminate of two or more sheets of the same or different polyurethanes.

In some embodiments the structural layer polyurethane comprises an oriented polyurethane.

In some embodiments the oriented polyurethane comprises a biaxially oriented polyurethane.

In some embodiments the oriented polyurethane is annealed.

The structural layer should be flexible enough to conform to the shape of the foam layers. The structural layer may be composed of one or more layers of polyurethane.

The structural layer may be biodegradable or non-biodegradable.

The structural layer may be a woven or non-woven layer of fibres as may be obtained for example by electrospinning.

The structural layer may be formed by melt pressing.

The structural layer may be formed by casting a film.

The structural layer may be subjected to orientation either in one direction or in two directions.

The structural layers provide strength to the tissue repair laminate. In a preferred embodiment oriented structural layers provide high strength to the tissue repair laminate.

Structural layers of 50 to 400 μm thickness offer a good balance between strength (increases with thickness), permeability (decreases with thickness) and handling (stiffer as it gets thicker). Additionally, the mass of the structural layer may become too high compared to the mass of the foam layers if it is too thick.

The tissue repair laminate may comprise a biocompatible and/or biodegradable adhesive located between the foam layers and the structural layer.

In other embodiments, no adhesive may be utilised and the structural layer may be fused directly onto the foam layers.

Structural Layer Polyurethane

The structural layer may comprise a biodegradable polyurethane. The structural layer may be derived from one or more polyols, one or more isocyanates and one or more chain extenders. The chain extenders may be biodegradable or non-degradable. Preferably, the chain extenders comprise biodegradable chain extenders.

The structural layer polyurethane may be derived from: one or more chain extenders represented by formula (1) or formula (2)

(1)

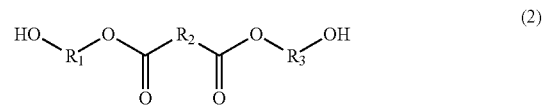

(2)

wherein $R_1$, $R_2$ and $R_3$ are independently selected from optionally substituted $C_{1-20}$ alkylene and optionally substituted $C_{2-20}$ alkenylene;
one or more aliphatic polyester polyols; and
one or more aliphatic diisocyanates.

The structural layer polyurethane may have a number average molecular weight ($M_w$) up to 200,000 Daltons, or up to 150,000 Daltons, or up to 100,000 Daltons, or up to 60,000 Daltons, or up to 40,000 Daltons, or up to 20,000 Daltons.

The structural layer polyurethane may have a number average molecular weight ($M_w$) between 2,000 and 200,000 Daltons, or between 5,000 and 150,000 Daltons or between 10,000 and 100,000 Daltons or between 20,000 and 100,000 Daltons or between 2,000 and 60,000 Daltons, or between 2,000 and 40,000 Daltons or between 2,000 and 20,000 Daltons.

The polyurethane may have a number average molecular weight ($M_n$) up to 100,000 Daltons, or up to 75,000 Daltons, or up to 50,000 Daltons, or up to 30,000 Daltons, or up to 20,000 Daltons, or up to 10,000 Daltons. Preferably, the number average molecular weight of the polyurethane is between 50,000 and 100,000 Daltons.

The polyurethane may have a polydispersity ($M_w/M_n$) between 1.0 and 4.0, or between 1.0 and 3.5, or between 1.5 and 3.0. Preferably the polydispersity is between 1.0 and 2.0.

Structural Layer Polyols

The polyols may comprise one or more polyester polyols.

The polyols may have a molecular weight between about 200 and about 2,000 Daltons, or between about 200 and about 1,500 Daltons, or between about 200 and about 1,300 Daltons.

The polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The polyols may have a molecular weight of less than 500 Daltons or less than 400 Daltons or less than 350 Daltons, or less than 300 Daltons.

The polyols may be in the liquid state at 20° C. and atmospheric pressure. Alternatively, the polyols may be in the solid state at 20° C. and atmospheric pressure.

The polyols may be derived from one or more diol initiators and one or more hydroxy acids, diacids or cyclic esters and combinations thereof.

In one embodiment the polyol may be derived from one or more diol initiators and at least one hydroxy acid.

In one embodiment the polyol may be derived from one or more diol initiators and at least one diacid.

In one embodiment the polyol may be derived from one or more diol initiators and at least one cyclic ester.

In one embodiment the polyol may be derived from one or more diol initiators, at least one hydroxy acid and at least one diacid.

In one embodiment the polyol may be derived from one or more diol initiators, at least one hydroxy acid and at least one cyclic ester.

In one embodiment the polyol may be derived from one or more diol initiators, at least one diacid and at least one cyclic ester.

In one embodiment the polyol may be derived from one or more diol initiators, at least one hydroxyl acid, at least one diacid and at least one cyclic ester.

Non-limiting examples of the one or more diol initiators include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof. Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof. The polyols may be prepared via a ring-opening polymerisation reaction or a condensation reaction or via both a ring-opening polymerisation reaction and a condensation reaction.

Structural Layer Chain Extenders

In some embodiments R1, R2 and R3 of formulae (1) and (2) are independently selected from optionally substituted C1-6 alkylene and optionally substituted C2-6 alkenylene.

The term "optionally substituted" refers to a group which may or may not be further substituted with one or more groups selected from C1-6 alkyl, C2-6 alkenyl, C2-6 alkynyl, halo, halo C1-6alkyl, halo C2-6 alkenyl, halo C2-6 alkynyl, hydroxy, C1-6 alkoxy, C2-6 alkenyloxy, halo C1-6 alkoxy, haloalkenyloxy, nitro, nitro C1-6 alkyl, nitro C2-6 alkenyl, nitro C-6 alkynyl, nitroheterocyclyl, amino, C1-6 alkylamino, C1-6 dialkylamino, C2-6 alkenylamino, C2-6 alkynylamino, acyl, alkenylacyl, alkynylacyl, acylamino, diacylamino, acyloxy, C1-6 alkylsulphonyloxy, heterocyclyl, heterocyclyloxy, heterocyclylamino, haloheterocyclyl, C1-6 alkylsulphenyl, carboalkoxy, mercapto, C1-6 alkylthio, acylthio, phosphorus-containing groups and the like. Preferred optional substituents are methyl, ethyl, propyl, butyl, and phenyl.

The chain extender of formula (1) or formula (2) is preferably hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer and mixtures thereof.

The chain extender of formula (1) of formula (2) may be prepared from one or more diols and one or more hydroxy acids and/or cyclic esters.

Non-limiting examples of the one or more diols include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof.

The polyurethane may further comprise one or more aliphatic polyol chain extenders which are hydrolytically non-degradable under in vivo conditions. For example, the polyurethane may further comprise one or more diol chain extenders which do not contain ester functionality in their backbones. Preferably, the non-degradable chain extender is an alkane diol having up to 30 carbon atoms, for example, ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and mixtures thereof.

Structural Layer Diisocyanates

The aliphatic diisocyanate is preferably 4,4'-methylene dicyclohexyl diisocyanate (HMDI), 1,6-hexane diisocyanate (HDI), 1,4-butane diisocyanate (BDI), L-lysine diisocyanate (LDI), ethyl-L-lysine diisocyanate (ELDI), methyl-L-lysine diisocyanate (MLDI), 2,4,4-trimethylhexamethylenediisocyanate, other similar diisocyanates, and mixtures thereof.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used. Combinations of isocyanates may be used and may in some instances be preferable—for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Structural Layer Polyurethane Degradation

The polyurethane may contain hard and soft segments. The ratio of hard to soft segment influences the melting point of the polyurethane.

The hard segment content (% HS) of the polyurethane (that is, the combined content of the components derived from the chain extender of formula (1) or formula (2) and isocyanate, expressed by weight percentage) may range from 2 to 100 wt. %, or from 5 to 80 wt %, or from 10 to 70 wt %.

The soft segment content (% SS) of the polyurethane (that is, the percentage by weight of the components derived from the polyester polyol) may range from 5-98%, and in some embodiments, is at least 25% or at least 40%.

In some embodiments the polyurethane comprises hard and soft segments wherein the hard segment content (% HS) of the polyurethane is less than 60%, preferably between 30 and 60%.

The amount of chain extender of formula (1) or formula (2) in the polyurethane may be varied to vary the non-degradable length of continuous urethane in the hard segment. For example, the non-degradable length of the hard segment may have a molecular weight between 100 and 10,000 Daltons, or between 200 and 5,000 Daltons, or between 400 and 2,000 Daltons, or between 200 and 700 Daltons or between 320 and 700 Daltons.

The structural layer polyurethane may degrade, under the conditions of ASTM F1635, such that the number average molecular weight ($M_n$) of the polyurethane decreases and/or the mass of the structural layer decreases by between 10% and 90% in a period of one year or less.

The structural layer polyurethane may be in vivo degradable. The polyurethane may be degradable at temperatures between 35 and 42° C.

Alternatively, the number average molecular weight ($M_n$) of the structural layer polyurethane and/or the mass of the structural layer may decrease by between 10% and 90% in a period of eleven months or less, or ten months or less, or nine months or less, or eight months or less, or seven months or less, or six months or less, or five months or less, or four months or less, or three months or less, or two months or less, or one month or less, under the conditions of ASTM F1365.

The rate of degradation, under the conditions of ASTM F1635, may be controlled through varying the nature and ratios of the components of the polyurethane. Accordingly, the polyurethane may be designed to degrade within a specific time period. This is advantageous in providing materials that are partially, fully, or substantially fully degradable in a specific time period, for example, when the functional aspects of the polyurethane are no longer required.

Melting Point

The melting point of the polyurethane of the structural layer may be between 60° C. and 190° C. The melting point may be between 60° C. and 180° C., or between 60° C. and 170° C., or between 60° C. and 160° C., or between 60° C. and 150° C., or between 60° C. and 140° C., or between 60° C. and 130° C., or between 60° C. and 120° C., or between 60° C. and 110° C., or between 60° C. and 100° C., or between 60° C. and 100° C., or between 60° C. and 90° C., or between 60° C. and 80° C., or between 60° C. and 70° C.

Where a clear melting transition occurs the melting point may be determined by differential scanning calorimetry. Other techniques know to those skilled in the art, such as dynamic mechanical thermal analysis, may also be utilised.

Preparation of the Laminate

The structural layer may be laminated to the foam layers by a combination of heat and pressure.

The structural layer may be laminated to the foam layers so as there are substantially no gaps (for example, air bubbles) between the materials.

The foam layers and the structural layers may be of substantially equal dimensions of length and width. The structural layer may be of smaller or larger dimensions of length and/or width than the foam layers.

The foam layers may have the same or different dimensions of length and/or width.

The structural layers may have the same dimensions of length and width.

The foam layers may have the same or different thicknesses.

The structural layers may have the same or different thicknesses.

The structural layers may be laminated to the foam layers through an interaction between the materials through the application of heat or pressure or a combination of heat and pressure. Alternatively, the structural layers may be covalently bonded to the foam layers. In an alternative and/or additional embodiment, the structural layers may be laminated to the foam layers with the aid of a suitable adhesive according to any of the aforementioned embodiments.

Accordingly, in another aspect of the present disclosure there is provided a method of preparing a tissue repair laminate comprising the steps of:
  (a) melt pressing a polyurethane to form a structural layer, said structural layer having first and second oppositely facing major surfaces;
  (b) applying a first polyurethane foam layer to the first major surface of the structural layer; and (c) fusing the foam layer and the structural layer together through the application of heat to the second major surface of the structural layer;

(d) applying a second polyurethane foam layer to the second major surface of the structural layer.

In some embodiments steps (c) and (d) may be performed concurrently.

In some embodiments steps (a) through (d) may be performed concurrently, for example, by using a calendering process.

The melt pressing may be performed at a temperature between 100 and 200° C.

The melt pressing may be performed at a pressure of up to 30 t.

The melt pressing may be performed between two smooth sheets. The sheets may be substantially smooth although some degree of surface texturing is acceptable. The melt pressing may be performed between two PTFE sheets, for example glass fibre reinforced PTFE sheets.

The fusing may be performed in the absence of applied pressure.

The fusing may be performed by applying heat to the second major surface of the structural layer, for example by exposing the second major surface to a temperature between 100 and 200° C.

The fusing may be performed for a time between 5 seconds and 5 minutes, preferably between 15 seconds and 90 seconds.

The structural layer may, alternatively, be applied to the foam layer by spraying or spreading.

In other embodiments the structural layer may be formed by other thermal processing methods known in the art such as, for example, cast extrusion and blown film extrusion.

In other embodiments the foam may be bonded or fused to the structural layer by calendering with heat or with the use of solvents or using ultrasonic means.

Accordingly, the structural layer may be bonded to the foam layer through ultrasonic welding. This is a particularly useful method of bonding the layers where an oriented structural layer is utilized.

Accordingly, in another aspect of the present disclosure there is provided a method of preparing a tissue repair laminate comprising the steps of:
(a) providing an oriented structural layer, said structural layer having first and second oppositely facing major surfaces;
(b) applying a first polyurethane foam layer to the first major surface of the structural layer;
(c) applying a second polyurethane foam layer to the second major surface of the structural layer; and
(d) bonding the foam layers and the structural layer together using ultrasonic welding.

Various adhesives may be utilized to fix the structural layer to the foam layers. The adhesive layer may be a confluent layer or discontinuous layer. Suitable adhesives include, but are not limited to, solvent-based adhesives, latex adhesives, pressure-sensitive adhesives, hot-melt adhesives, and reactive adhesives, such as a biodegradable or non-biodegradable thermoset polyurethane reactive mixture. Suitable pressure-sensitive adhesives include, but are not limited to, pressure-sensitive adhesives made from acrylics, natural latexes, styrene-butadiene rubbers, and reclaimed rubbers. Suitable hot-melt adhesives include, but are not limited to, polyamides, polyolefins, and poly(ethylene-co-vinyl acetate).

In one embodiment, the structural layer may itself be an adhesive. In other embodiments, no adhesive may be utilised—the structural layer is melted directly onto the foam layers.

In another aspect of the present disclosure there is provided use of a tissue repair laminate as herein disclosed in the repair of a tissue or muscle wall defect.

In another aspect of the present disclosure there is provided a method of repairing a tissue or muscle wall defect, comprising:
providing a tissue repair laminate as herein disclosed;
securing the laminate to the defect.

In another aspect, a method of repair of tissue damage in a subject in need thereof is provided. The method comprises surgically implanting the herein disclosed tissue repair laminate into a site of the tissue damage in the subject.

The damage may comprise, for example, a hernia, a ventral abdominal wall hernia, a rotator cuff injury, a pelvic organ prolapse, or a uro-gynecological injury. The site of the damage may be, for example, a soft tissue, a mesenchymal tissue, an intraperitoneal tissue, a rotator cuff tissue, a pelvic tissue, or a uro-gynecological tissue. The intraperitoneal tissue may be, for example, a ventral abdominal wall tissue. The rotator cuff tissue may be, for example, a rotator cuff tendon. The pelvic tissue may be, for example, a bladder tissue. The uro-gynecological tissue may be, for example, a urethral tissue. Thus, for example, the method may comprise surgically implanting the tissue repair laminate into a site, e.g. an intraperitoneal tissue, such as a ventral abdominal wall tissue, of a hernia, e.g. a ventral abdominal wall hernia, in the subject. Also for example, the method may comprise surgically implanting the tissue repair laminate, e.g. a rotator cuff repair laminate, into a site, e.g. a rotator cuff tissue, such as a rotator cuff tendon, of a rotator cuff injury in the subject. Also for example, the method may comprise surgically implanting the tissue repair laminate, e.g. a pelvic organ prolapse repair laminate, into a site, e.g. a pelvic tissue, such as a bladder tissue, of a pelvic organ prolapse in the subject. Also for example, the method may comprise surgically implanting the tissue repair laminate, e.g. a uro-gynecological reconstruction laminate, into a site, e.g. a uro-gynecological tissue, such as a urethral tissue, of a uro-gynecological injury in the subject.

The tissue repair laminates may also be useful in reinforcing tissues in surgical procedures such as abdominoplasty, breast reconstruction, midline closures, lateral closures, hernia repair, retrorectus hernia repair, Rives-Stoppa procedures, incisional hernias, cosmetic surgery, and the like.

Further features and advantages of the present disclosure will be understood by reference to the following drawings and detailed description.

DESCRIPTION OF PREFERRED EMBODIMENTS

Figure 1:
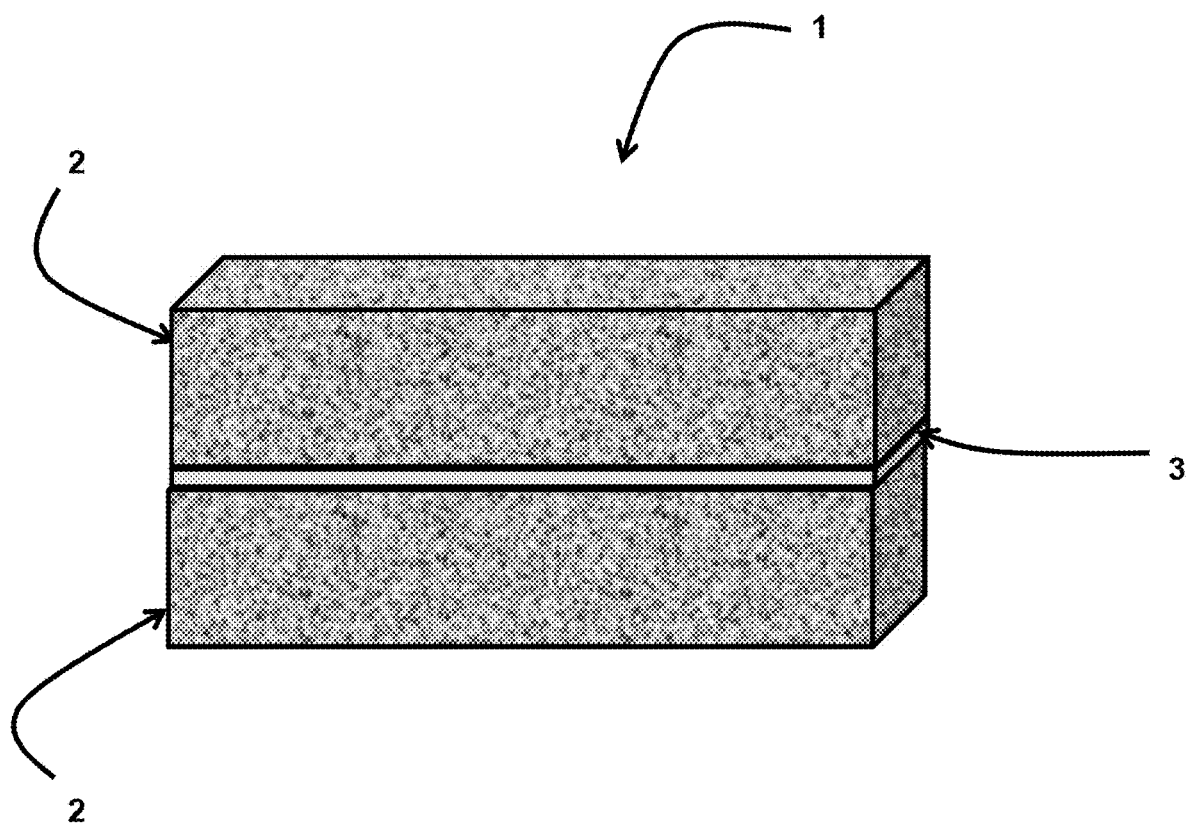
FIG. 1 illustrates a tissue repair laminate according to an embodiment of the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to 'chain extender' may include more than one chain extenders, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless defined otherwise, all technical and scientific terms used herein have the meaning commonly understood by a person skilled in the art to which this disclosure belongs.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The primary components and features used in the preparation of one or more embodiments of the tissue repair laminate as herein disclosed are discussed in detail in the following sections.

In one embodiment the present disclosure provides a tissue repair laminate wherein the polyurethane in the structural layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates;
wherein the polyurethane in the structural layer has a melting point between 60° C. and 190° C.; and
wherein the polyurethane in the structural layer and the foam layer degrade, under the conditions of ASTM F1635, such that the number average molecular weight ($M_n$) of the polyurethane of the structural layer and/or the mass of the foam layer independently decreases by between 10% and 90% in a period of one year or less.

In one embodiment the present disclosure provides a tissue repair laminate wherein the polyurethane in the structural layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane in the structural layer has a melting point between 60° C. and 190° C.; and
wherein the polyurethane in the structural layer and the foam layer degrade, under the conditions of ASTM F1635, such that the number average molecular weight ($M_n$) of the structural layer polyurethane and/or the mass of the foam layer independently decreases by between 10% and 90% in a period of one year or less.

In one embodiment the present disclosure provides a tissue repair laminate wherein the polyurethane in the structural layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid and/or cyclic ester; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane in the structural layer has a melting point between 60° C. and 190° C.; and
wherein the polyurethane in the structural layer and the foam layer degrade, under the conditions of ASTM F1635, such that the number average molecular weight ($M_n$) of the structural layer polyurethane and/or the mass of the foam layer independently decreases by between 10% and 90% in a period of one year or less.

In one embodiment the present disclosure provides a tissue repair laminate wherein the polyurethane in the structural layer is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid, diacid or cyclic ester, or combinations thereof, wherein the one or more diol initiators is selected from ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and combinations thereof and wherein the at least one hydroxy acid is selected from 1-lactic acid, d-lactic acid, d,l-lactic acid, mandelic acid, phenyl-lactic acid, valeric acid or glycolic acid; wherein the one or more diacids is selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and wherein the cyclic ester is selected from ε-caprolactone, glycolide, lactide, mandelide, and ρ-dioxanone; and one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;

wherein the polyurethane in the structural layer has a melting point between 60° C. and 190° C.; and wherein the polyurethane in the structural layer and the foam layer degrade, under the conditions of ASTM F1635, such that the number average molecular weight ($M_n$) of the structural layer polyurethane and/or the mass of the foam layer independently decreases by between 10% and 90% in a period of one year or less.

Bioactive Substances

Bioactive substances may optionally be added to the polyurethanes of the foam layer, the structural layer or both layers.

The bioactive substance may be formulated with the polyurethane to form a composition. The formulation may be facilitated by, for example, melt processing, additive manufacturing or dissolution in an appropriate solvent.

Bioactive substances may be synthetic molecules, biomolecules, or multimolecular entities and include, but are not limited to, enzymes, organic catalysts, ribozymes, organometallics, proteins, glycoproteins, peptides, polyamino acids, antibodies, nucleic acids, steroidal molecules, antibiotics, silver, silver oxide, antivirals, antimycotics, anticancer agents, analgesic agents, antirejection agents, immunosuppressants, cytokines, carbohydrates, oleophobics, lipids, extracellular matrix and/or its individual components, demineralized bone matrix, hydroxyapatite, tricalcium phosphate, pharmaceuticals, chemotherapeutics, and therapeutics. Cells and non-cellular biological entities, such as viruses, virus vectors and prions can also be bioactive substances. The bioactive substances may be chemically bonded to the polyurethane.

The biological effect in humans or animals is for medical, therapeutic, cosmetic and veterinary purposes, and encompasses pharmaceuticals including drugs, cosmeceuticals, nutraceuticals, and nutritional agents. It will be appreciated that some of bioactive compounds can be classified in more than one of these classes.

A wide range of bioactive substances may be incorporated into the presently disclosed polyurethanes and may be consequently delivered with the tissue repair laminates as herein disclosed.

Examples include, but are not limited to, cardiovascular drugs, in particular antihypertensive agents (e.g. calcium channel blockers or calcium antagonists) and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; α-blockers; β-blockers; sodium channel blockers; potassium channel blockers; β-adrenergic agonists; platelet inhibitors; angiotensin antagonists; anticoagulants; thrombolytic agents; treatments for bleeding; treatments for anaemia; thrombin inhibitors; antiparasitic agents; antibacterial agents; insulin; human growth hormone and peptides; vaccines; anti-inflammatory agents, in particular non-steroidal anti-inflammatory agents (NSAIDs), more particularly COX-2 inhibitors; steroidal anti-inflammatory agents; prophylactic anti-inflammatory agents; anti glaucoma agents; mast cell stabilisers; mydriatics; agents affecting the respiratory system; allergic rhinitis pharmaceuticals; a adrenergic agonists; corticosteroids; chronic obstructive pulmonary disease pharmaceuticals; xanthine-oxidase inhibitors; anti-arthritis agents; gout treatments; autacoids and autacoid antagonists; anti mycobacterial agents; antifungal agents; antiprotozoal agents; anthelmintic agents; antiviral agents especially for respiratory, herpes, cyto-megalovirus, human immunodeficiency virus and hepatitis infections; treatments for leukaemia and Kaposi's sarcoma; pain management agents in particular opioids, anaesthetics and analgesics; neuroleptics; sympathomimetic pharmaceuticals; adrenergic agonists; drugs affecting neurotransmitter uptake or release; anticholinergic pharmaceuticals; anti haemorrhoid treatments; agents to prevent or treat radiation or chemotherapeutic effects; lipogenesis drugs; fat reducing treatments; anti-obesity peptides; anti-obesity agents such as lipase inhibitors; sympathomimetic agents; treatments for gastric ulcers and inflammation such as proton pump inhibitors; prostaglandins; VEGF inhibitors; antihyperlipidemic agents, in particular statins; drugs that affect the central nervous system (CNS) such as antipsychotic, antiepileptic and anti-seizure drugs (anticonvulsants), psychoactive drugs, stimulants, antianxiety and hypnotic drugs, antidepressant drugs; anti Parkinson's pharmaceuticals; hormones and fragments thereof such as sex hormones; growth hormone antagonists; gonadotropin releasing hormones and analogues thereof; steroid hormones and their antagonists; selective estrogen modulators; growth factors; anti diabetic pharmaceuticals such as insulin, insulin fragments, insulin analogues, glucagon like peptides and hypoglycaemic agents; H1, H2, H3 and H4 antihistamines; peptide, protein, polypeptide, nucleic acids and oligonucleotide pharmaceuticals; analogues, fragments and variants of natural proteins, polypeptides, oligonucleotides and nucleic acids and such like compounds; agents used to treat migraine headaches; asthma pharmaceuticals; cholinergic antagonists; glucocorticoids; androgens; antiandrogens; inhibitors of adrenocorticoid biosynthesis; osteoporosis treatments such as biphosphonates; antithyroid pharmaceuticals; cytokine agonists; cytokine antagonists; anticancer drugs; antialzheimer drugs; HMG-CoA reductase inhibitors; fibrates; cholesterol absorption inhibitors; HDL cholesterol elevating agents; triglyceride reducing agents; anti-ageing or anti-wrinkle agents; precursor molecules for the generation of hormones; proteins such as collagen and elastin; antibacterial agents; anti acne agents; antioxidants; hair treatments and skin whitening agents; sunscreens, sun protectants and filters; variants of human apolipoprotein; precursor molecules for generation of hormones; proteins and peptides thereof; amino acids; plant extracts such as grape seed extract; DHEA; isoflavones; nutritional agents including vitamins, phytosterols and iridoid gylcosides, sesquiterpene lactones, terpenes, phenolic glycosides, triterpenes, hydroquinone derivatives, phenylalkanones; antioxidants such as retinol and other retinoids including retinoic acid and co enzyme Q10; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, or prevention of human and animal diseases such as allergy/asthma, arthritis, cancer, diabetes, growth impairment, cardiovascular diseases, inflammation, immunological disorders, baldness, pain, ophthalmological diseases, epilepsy, gynaecological disorders, CNS diseases, viral infections, bacterial infections, parasitic infections, GI diseases, obesity, and haemological diseases.

It is to be understood that pharmaceutically, nutraceutically or cosmeceutically acceptable derivatives of bioactive substances are included within the scope of the present disclosure.

The term "pharmaceutically, nutraceutically or cosmeceutically acceptable derivatives" includes, but is not limited to, pharmaceutically, nutraceutically or cosmeceutically acceptable salts, esters, salts of such esters, ethers, or any other derivative including prodrugs and metabolites, which upon administration to a subject (e.g. patient, human or animal) in need is capable of providing, directly or indirectly, a bioactive substance as otherwise described herein.

As used herein, the term "pharmaceutically, nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically, nutraceutically or cosmeceutically acceptable salts are well known in the art. For example, S. M. Berge, et al. describe pharmaceutically, nutraceutically or cosmeceutically acceptable salts in detail in J. Pharmaceutical Sciences, 66:1-1 9, 1977.

Examples of pharmaceutically, nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as-aceticacid, oxalic acid, maleic acid, tartaric acid citric acid, succinic acid, or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2 hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically, nutraceutically or cosmeceutically acceptable ester" refers to esters which are hydrolysed in vivo and include those that break down readily in the human body to leave the parent compound or a salt thereof. Suitable ester groups include, for example, those derived from pharmaceutically, nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically, nutraceutically or cosmeceutically acceptable prodrugs" as used herein includes those prodrugs of the biologically active substances which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the biologically active substances.

The term "prodrug" refers to compounds that are rapidly transformed in vivo to yield a parent compound, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The present disclosure is further not limited solely to the administration of one biologically active substance: more than one biologically active substance or other therapeutic compounds may be incorporated into the foam layer and/or structural layer.

Degradation

The polyurethanes of either the foam layer or the structural layer or both layers of the tissue repair laminate of the present disclosure may be designed to degrade in vivo or under in vivo conditions at controlled rates. The polyurethanes may be degradable at temperatures between 35 and 42° C.

In some embodiments the number average molecular weight ($M_n$) of the structural layer polyurethane and the mass of the foam layer may independently decrease by between 20% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 30% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 40% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 50% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 60% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 70% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 80% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 20% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 30% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 40% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 50% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the structural layer polyurethanes and the mass of the foam layer may independently decrease by between 60% and 70% in a period of eleven months or less, or ten months or less, or nine months or less, or eight months or less, or seven months or less, or six months or less, or five months or less, or four months or less, or three months or less, or two months or less, or one month or less.

FIG. 1 illustrates a tissue repair laminate (1) according to an embodiment of the present disclosure comprising foam layers (2) and structural polyurethane layer (3)

Figure 2:
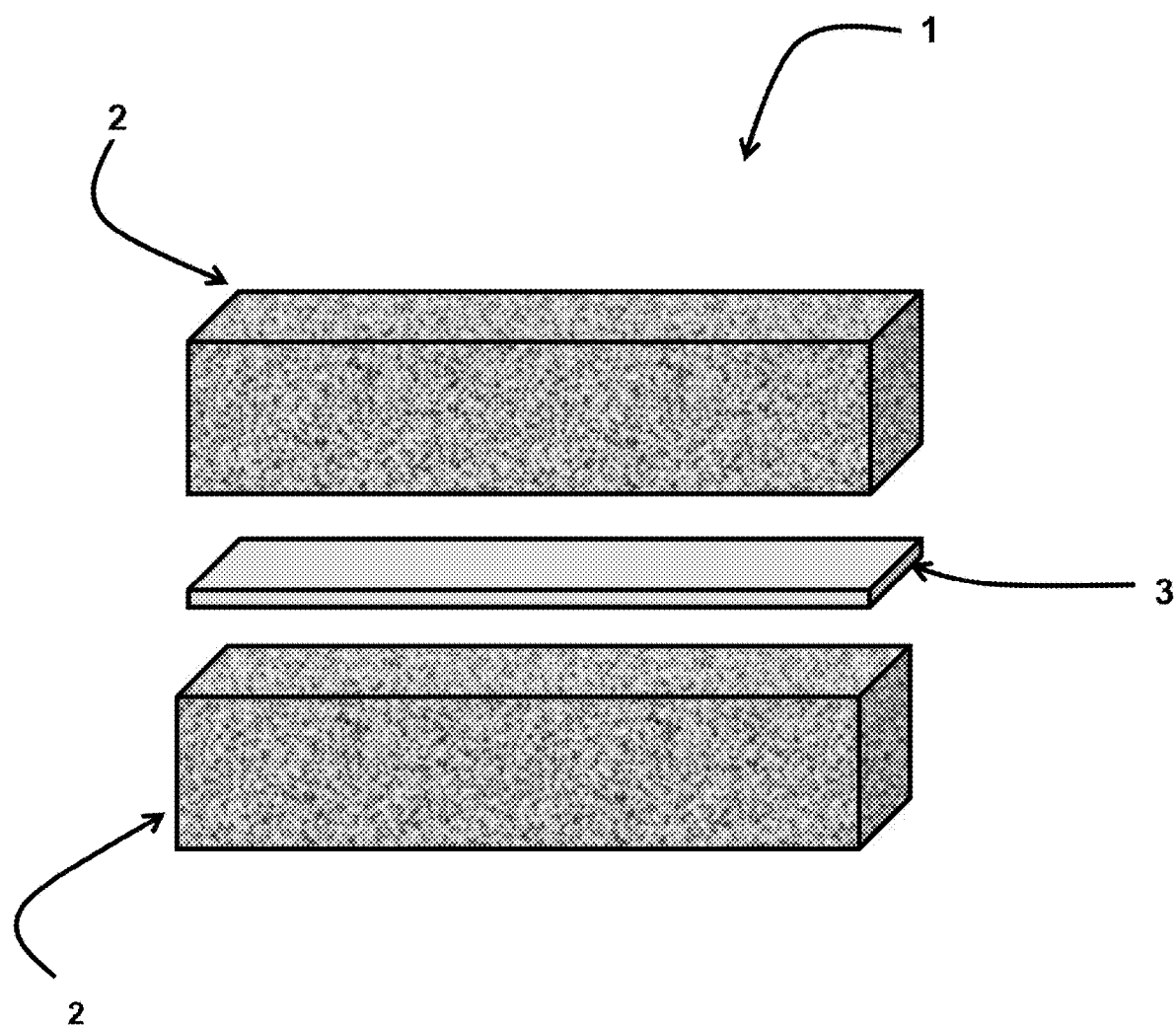
FIG. 2 illustrates an exploded view of the tissue repair laminate of FIG. 1.

FIG. 2 illustrates an exploded view of tissue repair laminate (1) according to an embodiment of the present disclosure comprising foam layers (2) and polyurethane structural layer (3).

Figure 3:
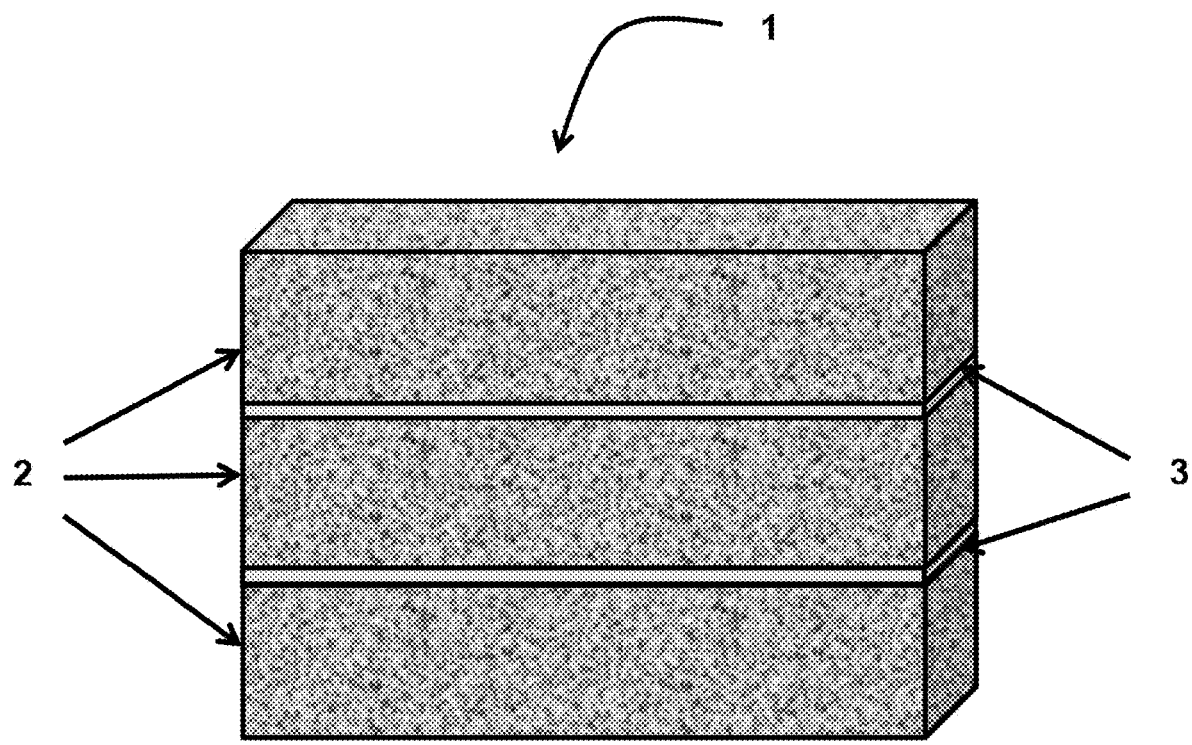
FIG. 3 illustrates a tissue repair laminate according to another embodiment of the present disclosure.

FIG. 3 illustrates a tissue repair laminate (1) according to another embodiment of the present disclosure comprising foam layers (2) and structural polyurethane layers (3)

Figure 4:
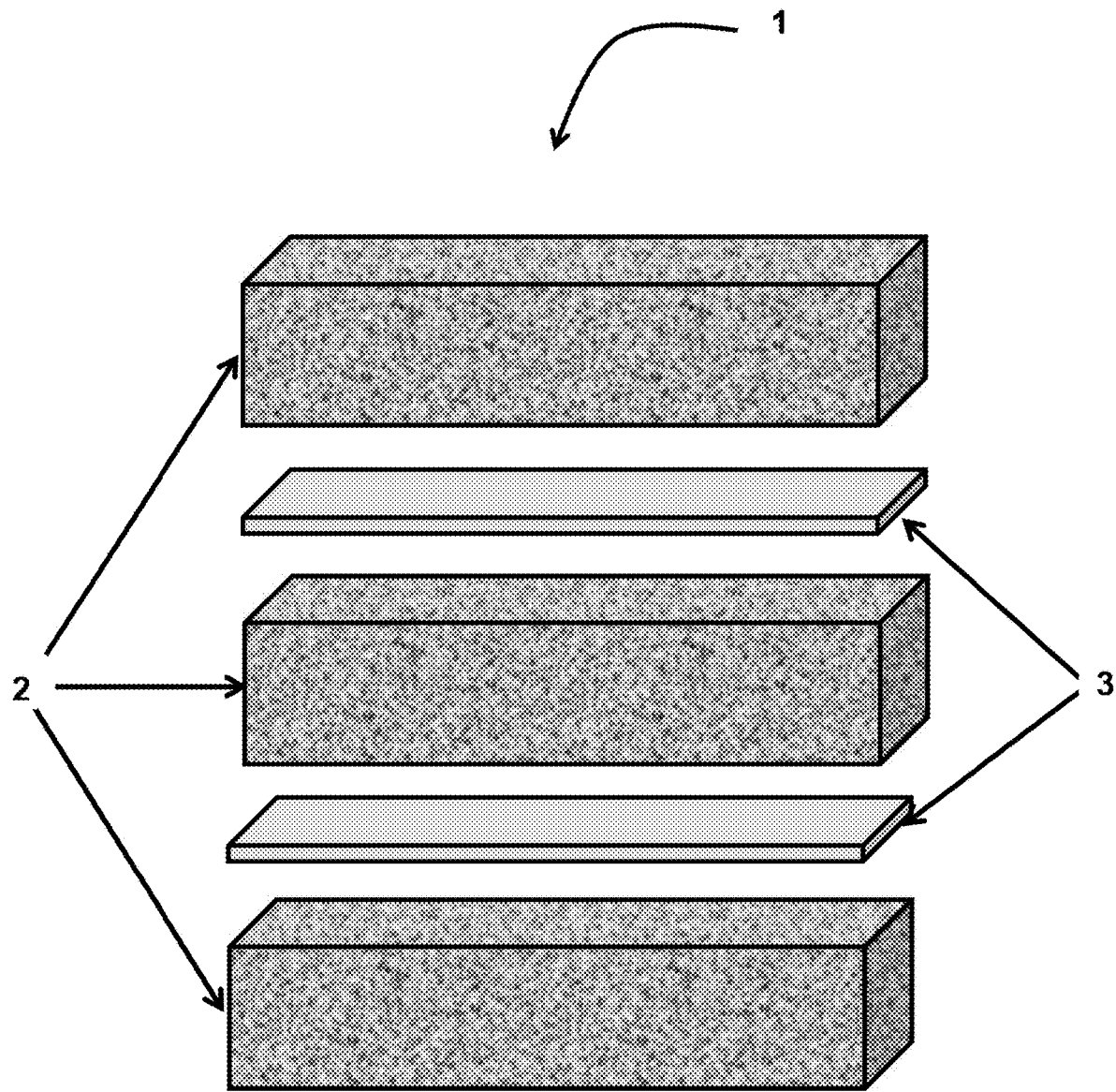
FIG. 4 illustrates an exploded view of the tissue repair laminate of FIG. 3.

FIG. 4 illustrates an exploded view of tissue repair laminate (1) according to another embodiment of the present disclosure comprising foam layers (2) and structural layers (3).

The following Examples describe the preparation of the tissue repair laminates according to the present disclosure and are intended to illustrate the disclosure. The Examples are not to be construed as limiting in any way the scope of the present disclosure.

EXAMPLES

Foam Layer Preparation

A biodegradable polyurethane foam was prepared according to the present disclosure. The foam was cut into sheets of various thickness using conventional foam slicing equipment.

Structural Layer Preparation

Example 1: Polyol Synthesis

Polyols were prepared by condensation of L-lactic acid (LLA), ε-caprolactone (CL) and 1,4-butane diol (BDO). All components were weighed into a glass reactor fitted with stirring, nitrogen outgassing, a condenser, and a heat source. The temperature was set to between 130° C. and 210° C. and the stirring and nitrogen flow started. Water was removed from the vessel via the condenser as the reaction proceeded. The reaction was continued until completion as indicated by residual acid measurement at which point the polyol was cooled and stored for use.

Polyols of molecular weight of about 400 were prepared as above using weight ratios of LLA:CL of 30:70 along with BDO initiator.

In a specific example, 3887 g of 1,4-butane diol (BDO), 3953 g of 90% lactic acid, and 10520 g of ε-caprolactone were added to a reactor fitted with stirring, condenser and a nitrogen atmosphere. The mixture was heated at 200° C. and heating was removed once the acid number was 1.9 mg KOH/g.

Example 2: Chain Extender Synthesis

The chain extender was prepared by ring opening polymerisation of ε-caprolactone (CL) and 1,4-butane diol (BDO) in a 1:5 molar ratio. The temperature was set to between 130° C. and 210° C. with stirring and nitrogen. The reaction was continued until completion as indicated by gas chromatography (GC) analysis at which point the chain extender was cooled and stored for use.

In an example, 706.5 g ε-caprolactone and 2792.5 g BDO were added to a reactor fitted with heating and stirring. The mixture was heated at 200° C. until ε-caprolactone was no longer detectable by GC. GC testing of the product indicated 67.9% BDO, 26.7% dimer and 3.8% trimer.

Example 3: Prepolymer Synthesis 6000.5 g of the above prepared polyol was charged to a reactor fitted with stirring and nitrogen and 3467.5 g 1,6- hexane diisocyanate (HDI) added. The mixture was heated to 60° C. and the reaction exotherm reached 90° C. The mixture was then cooled to 60° C. and 128.27 g of the above prepared chain extender and 0.2 g catalyst added. The exotherm reached 82° C. The NCO content of the prepolymer was found to be 7.607%.

Example 4: Polymer Synthesis 9458.5 g of the above prepared prepolymer was weighed into a 20 litre container, and 771.5 g dry BDO added along with 0.7 g catalyst. The mixture was stirred and then poured into PTFE-lined trays and cured in an oven for a period of 2 hours at 120° C. The polymer was then granulated using a Zerma GSL 180/300 granulator.

Example 5: Polymer Synthesis (42% Hard Segment)

Under nitrogen and stirring, 3 kg of the polyol of Example 1 was combined with HDI (1.734 kg). BDO-CL (Example 2; 63.5 g) and organozinc catalyst were added with heating to complete a prepolymer and the isocyanate content assayed. This was then chain extended using BDO (407.6 g) and further zinc catalyst. The stirred mixture was then poured into PTFB-lined trays and cured in an oven for 2 hours at 120° C. The cured polymer was then granulated.

Example 6: Cast Film for Structural Layer

Dried granulated polymer from Example 5 was extruded on a small-scale cast film line equipped with extruder and chill rolls to provide a continuous film of between 235 and 420 μm thickness. Temperature during extrusion was between 160-185° C., and a lower temperature in the feeding zone.

Example 7: Stretching—Machine Direction Orientation (MDO)

Cast film from Example 6 (300 μm thickness) was run through a continuous stretching machine (MDO) and stretched with heat (from 40° C. to 90° C.). Stretch ratios of up to 1:5.5 were used and the measured residual stretching ratios were between 1:2.3 and 1:4. The stretching was conducted in two manners—using a roll of prepared film, and also in series with the immediate output of the cast film line being fed into the continuous stretcher as a continuous process. The film was collected on separate rolls for each condition.

Example 8: Melt Pressed Structural Layer

Polymer granules prepared as in Example 4 were melt pressed between glass fibre-reinforced PTFE sheets at 175° C., 10 t pressure on a Carver press, to form a film 0.2 mm thick sheet.

Example 8: Laminate Preparation

A 1 mm thick foam sheet prepared as above was applied to the top of the melt-pressed structural layer of Example 8 and heated on a melt-press platen without pressure at 175° C. for 45 seconds to bond the two layers together. A second 1 mm thick foam sheet was applied to the exposed surface of the structural layer to form a laminate comprising a structural layer sandwiched between two foam layers.

The properties of the laminate may be measured using industry standard methods using an Instron 5566 mechanical testing machine. Results are collected in Table 1.

TABLE 1

| Material | Suture retention (N) | UTS (machine direction) (N/cm) | Ball burst strength (N/cm) | Tear resistance (N) |
| --- | --- | --- | --- | --- |
| Laminate (Dry) | ~40 | ~50 | ~170 | ~20 |
| Laminate (Wet) | ~40 | ~50 | ~90 | ~20 |

Example 9: Ultrasonic Welding

A three-layer laminate (foam-film-foam) was prepared using film of Example 7 and annealed at 70° C. prior to use, and 2 mm thick foam (biodegradable polyester-urethane-urea thermoset foam).

The foam sheet was placed on top and bottom of the stretched and annealed film and welded together using an ultrasonic probe (40 kHz probe, Dukane IQ) with settings of 3 Joules per weld and 50 Amplitude. The sheets were welded with a 4 mm spot weld and in a square array of 14 mm spacing (centre to centre). Tensile specimens were prepared and tested on an Instron model 5566 (10 cm length, 2.6 cm width, 2 columns of welds per specimen, 50 mm gauge length, 500 mm/min). The welds were secure on both sides.

Figure 5:
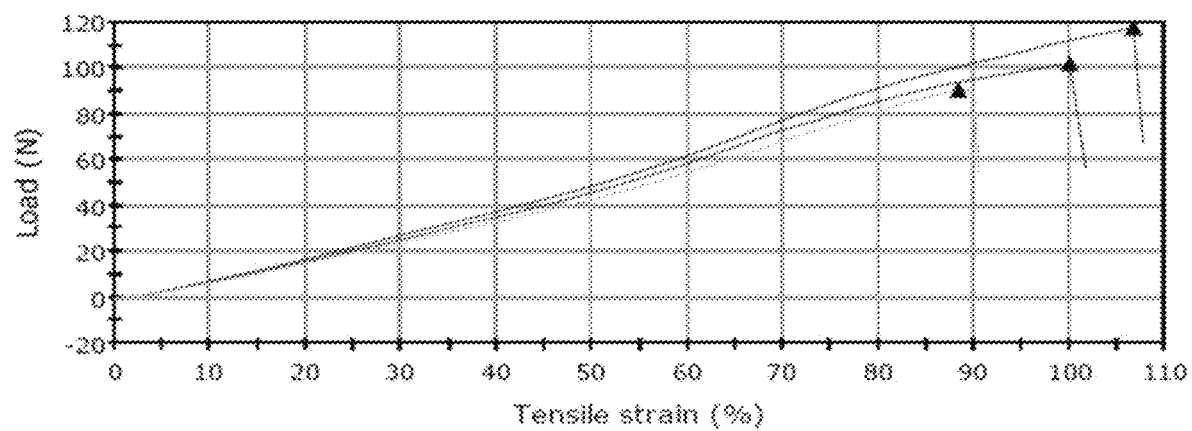
FIG. 5 illustrates the stress-strain curve of a laminate according to one embodiment of the present disclosure.

The average mechanical properties of the foam-film-foam laminate was as follows: Ultimate tensile strength 38.6 N/cm, Elongation 99%. FIG. 5 illustrates the stress strain curve of the ultrasonically-welded foam-film-foam laminate Comparative Example 1: Mechanical Test Results Mechanical tests were performed on foam layers absent the presence of the structural layer. The tests were performed on foam layers of 2 mm, 3 mm and 4 mm thickness, both wet and dry, and at high and low strain rates. Table 2 collects the results of Ball Burst Strength and Suture Retention.

TABLE 2

| Thickness and Condition | Ball burst strength (N/cm) | Suture retention (N) |
| --- | --- | --- |
| 2 mm, 300 mm/min, wet | 7 | 0.65 |
| 2 mm, 300 mm/min, dry | 21 | 1.43 |
| 3 mm, 300 mm/min, wet | 10 | 0.89 |
| 3 mm, 300 mm/min, dry | 28 | 2.14 |
| 4 mm, 300 mm/min, wet | 11 | 1.19 |
| 4 mm, 300 mm/min, dry | 36 | 2.35 |

Compared to the Ball Burst Strengths and Suture Retention Strengths of the laminates in Table 1, the foam layers absent a structural layer performed very poorly. Even foam layers of 4 mm thickness performed extremely poorly compared to the 1 mm foam layer laminated with a 200 μm structural layers.

Under in vivo conditions, the tissue repair laminate of the present disclosure indicated minimum shrinkage in any single surface area. For example, less than 5% shrinkage in any single surface area.

The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A tissue repair laminate comprising:
   (a) two or more biodegradable polyurethane foam layers; and
   (b) one or more structural layers;
      wherein the one or more structural layers each have a thickness in the range of from about 50 μm to about 500 μm, and are positioned between said foam layers;
      wherein the one or more structural layers consist essentially of biodegradable thermoplastic polyurethane and one or more apertures;
      wherein said foam layers comprise a pore structure configured for cellular infiltration, and the foam of said foam layers is a non-reticulated foam;
      wherein said tissue repair laminate shrinks due to formation of tissue less than 20% in any one surface area after 20 days under in vivo conditions following implantation of the tissue repair laminate;
      and wherein the structural layer polyurethane is derived from components including
      one or more chain extenders represented by formula (1) or formula (2)

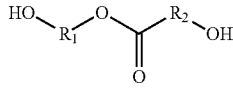

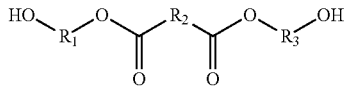

wherein $R_1$, $R_2$ and $R_3$ are independently selected from optionally substituted $C_{1-20}$ alkylene and optionally substituted $C_{2-20}$ alkenylene;
   one or more aliphatic polyester polyols; and
   one or more aliphatic diisocyanates.

2. The tissue repair laminate according to claim 1, wherein the two or more biodegradable polyurethane foam layers polyurethane is thermoset.

3. The tissue repair laminate according to claim 1, wherein said tissue repair laminate shrinks less than 15%, in any one surface area after 20 days under in vivo conditions.

4. The tissue repair laminate according to claim 1, wherein each layer of the two or more biodegradable polyurethane foam layers has a thickness between about 0.1 mm and about 10 mm.

5. The tissue repair laminate according to claim 1, wherein the foam layer has a thickness between about 0.3 mm and about 1 mm and the structural layer has a thickness between about 100 μm and about 300 μm.

6. The tissue repair laminate according to claim 1, wherein the average pore size of the pore structure is greater than 50 μm.

7. The tissue repair laminate according to claim 1, wherein each layer of the two or more biodegradable polyurethane foam layers degrades, under the conditions of ASTM F1635, such that the mass of each layer of the two or more biodegradable polyurethane foam layers decreases by between 10% and 90% in a period of one year or less.

8. The tissue repair laminate according to claim 1, wherein the polyurethane structural layer degrades, under the conditions of ASTM F1635, such that the number average molecular weight ($M_n$) of the polyurethane decreases by between 10% and 90% in a period of one year or less.

9. The tissue repair laminate according to claim 1, wherein said laminate has any one or more of the following features:
   (i) a suture retention strength of greater than 20 N;
   (ii) an ultimate tensile strength of greater than 20 N/cm;
   (iii) a ball burst strength of greater than 100 N/cm; and
   (iv) a tear resistance of greater than 10 N.

10. The tissue repair laminate according to claim 1, wherein each layer of the two or more biodegradable polyurethane foam layers is derived from one or more biodegradable polyols and one or more isocyanates.

11. The tissue repair laminate according to claim 1, wherein each layer of the two or more biodegradable polyurethane foam layers is derived from a mixture of one or more biodegradable polyols and one or more non-biodegradable polyols and one or more isocyanates.

12. The tissue repair laminate according to claim 10, wherein the biodegradable polyols are polyester polyols.

13. The tissue repair laminate according to claim 10, wherein the biodegradable polyols have a molecular weight of less than or equal to about 10,000 Daltons.

14. The tissue repair laminate according to claim 10, wherein the biodegradable polyols are derived from one or more polyol initiators and one or more hydroxy acids, diacids, cyclic esters, or combinations thereof.

15. The tissue repair laminate according to claim 11, wherein the non-biodegradable polyols are polyether polyols.

16. The tissue repair laminate according to claim 15, wherein the polyether polyol is selected from one or more of glycerol ethoxylate, glycerol propoxylate, glycerol ethoxylate-co-propoxylate, glycerol ethoxylate-block-propoxylate, pentaerythritol ethoxylate, pentaerythritol propoxylate and trimethylolpropane propoxylate.

17. The tissue repair laminate according to claim 1, wherein the structural layer polyurethane comprises an oriented polyurethane.

18. The tissue repair laminate according to claim 1, wherein the polyurethane structural layer has a number average molecular weight ($M_n$) between 2,000 and 200,000 Daltons.

19. The tissue repair laminate according to claim 1, wherein the polyols have a number average molecular weight ($M_n$) of less than or equal to about 10,000 Daltons.

20. The tissue repair laminate according to claim 1, wherein the polyol comprises a polyester polyol.

21. The tissue repair laminate according to claim 20, wherein the polyester polyol is derived from one or more diol initiators and one or more hydroxy acids, diacids or cyclic esters and combinations thereof.

22. The tissue repair laminate according to claim 1, wherein the structural layer polyurethane further comprises one or more aliphatic polyol chain extenders which are hydrolytically non-degradable under in vivo conditions.

23. The tissue repair laminate according to claim 1, wherein the structural layer further comprises one or more aliphatic polyol chain extenders which do not contain ester functionality in their backbones.

24. The tissue repair laminate according to claim 23, wherein the one or more aliphatic polyol chain extenders is an alkane diol having up to 30 carbon atoms.

25. The tissue repair laminate according to claim 1, wherein the isocyanate is an aliphatic diisocyanate is selected from the group consisting of 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate, ethyl-L-lysine diisocyanate (ELDI), methyl-L-lysine diisocyanate (MLDI), and mixtures thereof.

26. The tissue repair laminate according to claim 1, wherein $R_1$, $R_2$ and $R_3$ of formulae (1) and (2) are independently selected from substituted $C_{1-6}$ alkylene and substituted $C_{2-6}$ alkenylene.

27. The tissue repair laminate according to claim 1, wherein the chain extender of formula (1) or formula (2) is selected from the group consisting of hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer, lactic acid-ethylene glycol dimer and mixtures thereof.

28. The tissue repair laminate according to claim 1, wherein the polyurethane comprises hard and soft segments and wherein the hard segment content (% HS) of the polyurethane is between 2 to 100 wt. %.

29. The tissue repair laminate according to claim 1, wherein the laminate comprises one or more apertures which extend through each layer of the two or more biodegradable polyurethane foam layers and the one or more thermoplastic polyurethane structural layers.

30. A method of repairing a tissue or muscle wall defect, comprising providing a tissue repair laminate according to claim 1 and securing the laminate to the defect.

\* \* \* \* \*